United States Patent [19]

Maloney

[11] Patent Number: 5,212,476
[45] Date of Patent: May 18, 1993

[54] WIRELESS INTRAORAL CONTROLLER DISPOSED IN ORAL CAVITY WITH ELECTRODES TO SENSE E.M.G. SIGNALS PRODUCED BY CONTRACTION OF THE TONGUE

[76] Inventor: Sean R. Maloney, 405 Sondley Woods Pl., Asheville, N.C. 28805

[21] Appl. No.: 590,463

[22] Filed: Sep. 28, 1990

[51] Int. Cl.[5] .................... H09B 1/034; A61B 5/0488; A61B 5/0492; A61B 5/103
[52] U.S. Cl. ............................. 340/825.19; 128/642; 128/733; 128/777; 340/539; 455/100
[58] Field of Search ............. 128/641, 642, 732, 733, 128/774, 777, 905; 73/379; 623/24, 25; 433/32, 68, 69; 606/204, 204.35; 340/825.19, 407, 539; 455/100, 128; 381/70

[56] References Cited

U.S. PATENT DOCUMENTS

| | | | |
|---|---|---|---|
| 3,983,865 | 10/1976 | Shepard | 128/777 |
| 4,112,596 | 9/1978 | Fletcher et al. | 128/777 |
| 4,175,338 | 11/1979 | Takinishi et al. | 128/777 |
| 4,334,542 | 6/1982 | Takinishi et al. | 128/777 |
| 4,355,645 | 10/1982 | Mitani et al. | 128/777 |
| 4,550,427 | 10/1985 | Katz et al. | |
| 4,605,927 | 8/1986 | Katz et al. | 340/825.19 |
| 4,629,424 | 12/1986 | Lauks et al. | 128/777 |
| 4,669,477 | 6/1987 | Ober | 128/777 |
| 4,777,954 | 10/1988 | Keusch et al. | 128/641 |
| 4,783,656 | 11/1988 | Katz et al. | 340/825.19 |

FOREIGN PATENT DOCUMENTS 2457854 12/1974 Fed. Rep. of Germany ...... 128/733

OTHER PUBLICATIONS

"External Control of Rate, Recruitment, Synergy and Feedback in Paralyzed Extremities", Solomonow et al, *Orthopedics*, Jul. 1984.
Electrotactile Stimulation Relevant to Sensory-Motor Rehabilitation—A Process Report, Solomonow et al, *Prosthetics Research*, Spring 1980, vol. 17, No. 1.

*Primary Examiner*—Donald J. Yusko
*Assistant Examiner*—John Giust
*Attorney, Agent, or Firm*—Carter & Schnedler

[57] ABSTRACT

An intraoral controller senses electromyographic signals within the oral cavity which are produced as a result of movement and contraction of the tongue muscle. Active and reference electrodes pairs act as sensors for electromyographic signals which are processed into control signals. The electrodes are mounted on a substrate within the oral cavity. Signals from the electrodes are transmitted by telemetry or by wires to an electromyographic signal processor which is connected to a device to be controlled.

32 Claims, 6 Drawing Sheets

WIRELESS INTRAORAL CONTROLLER DISPOSED IN ORAL CAVITY WITH ELECTRODES TO SENSE E.M.G. SIGNALS PRODUCED BY CONTRACTION OF THE TONGUE

BACKGROUND OF THE INVENTION

This invention relates devices for providing control without the need of one's hands. More particularly it relates to intraoral control devices.

When high level spinal cord injured individuals lose the ability to control their upper extremities, they are left with no way to perform activities of daily living. Functional electrical stimulation of the muscles of the upper extremities and hands is currently being investigated as a means of allowing the high level quadriplegic to regain the use of their upper extremities and hands. However it is difficult to transmit the desired information for such stimulation from the brain, bypassing the spinal injury, directly to devices which provide the electrical stimulation. Furthermore control of movement in the upper extremities and hands when performing activities of daily living is a much more complex task than control of movement of lower extremities during ambulation. The simultaneous contraction of muscles of the hand, the wrist, and elbow while performing a complex movement makes their control very difficult. There is a constant need for complex proprioceptive kinesthetic and other sensory feedback to modify simultaneous muscle contractions.

Nonimpaired functions of a high quadriplegic are best utilized in order to control electrical stimulation of the arms and hands and other devices. Two functions which are not impaired as a result of a high level spinal injury are jaw movement and tongue movement. Even if electrical stimulation of muscles in the upper extremities and hands proves not to be completely successful, the high level quadriplegic still has the need to control other devices in order to function more independently.

Apparatus associated with the use of tongue or jaw movement are referred to as intraoral controllers. An attempt was made to develop an intraoral controller between 1966 and 1970 as part of a large research project to develop an external orthotic device to allow high quadriplegics to move their upper extremities. The project was conducted by a medical engineering research group at Rancho Los Amigos Hospital in Los Angeles, Calif. with Vernon L. Nichols MD being the principal investigator and the University of Michigan Dental School at Ann Arbor, Mich. with Major M. Ashe, DDS as the principal dental consultant. Six sets of magnetic flux sensitive resistors were used to control the velocity in a corresponding electrically powered arm brace which was also under development. The first attempt was to place the sensors on a partial dental plate in the mandible with movement of a magnet by the tongue. Implantation of the magnet into the tongue was tried on several dogs, however subsequent fibrosis around the magnet implant and a breakdown of its stainless steel coating became a problem. A second strategy was then tried by placing the 16 magnetic flux sensitive resistors on a maxillary partial dental plate with magnets placed on a similar mandibular partial denture. In the same project an attempt was also made to develop pressure sensitive sensors which could be activated by the tongue on a maxillary partial denture. None of those strategies proved successful in developing a useful intraoral controller.

In 1978, a device called a tongue activated computer controller (TACC) was developed by Daniel Fortune for a high level quadriplegic. The controller consisted of a set of ten ¼" diameter switches placed ¼" apart on a surface under the hard and soft palates. It was demonstrated that, with practice, the tongue could operate the switches with approximately 70% accuracy.

Another attempt at developing an intraoral controller was made at Stanford University in 1982 and 1983. The Stanford controller consisted of a palatial splint with two mircoswitches mounted on a bite block and a two axis piezoresistive transducer placed between the upper and lower teeth in a space below the hard palate. The microswitches were operated by jaw movement. The two axis transducer was operated by the tongue, however the transducer was quite large making it bulky and aesthetically unsatisfactory. Another attempt was also made at Stanford University using a series of microswitches on a palatial splint, however those switches experienced corrosion problems.

The patent literature reveals various attempts at intraoral controllers. U.S. Pat. Nos. 4,605,927 and 4,783,654 issued to Philip Katz et al show an intraoral control unit and system which utilizes on-off switches and which generate FM signals from inside the mouth to an external FM receiver which in turn operates a controller for controlling various appliances such as a television, lights and bed positions controls. Physical contact by the tongue is required to operate the Katz switches U.S. Pat. No. 4,629,424 issued to Lauks et al shows an intraoral ambient sensing device which utilizes a substrate having an FM transmitter attached thereto.

U.S. Pat. No. 4,728,812 issued to Sherif et al shows a oral machine controller operated by the teeth.

An article appearing in the *Proceedings of the 33rd Annual Conference on Engineering in Medicine and Biology*, 1980, Volume 22, by Swartz and Katz, discussed biofeedback devices for tongue placement evaluation therapy. In an article in the *Proceedings of the 29th Annual Conference on Engineering in Medicine and Biology of* 1976, Volume 18, by David J. Powner, a call system for quadriplegic patients is discussed.

OBJECTS OF THE INVENTION

It is therefore one object of this invention to provide an improved intraoral controller.

It is another object to provide an intraoral controller which provides amplitude and direction control.

It is another object to provide an improved intraoral controller which does not primarily rely on mechanical switches for its operation.

It is another object to provide a intraoral controller which is compact and easy to use.

It is still another object to provide an intraoral controller which is not readily visible and does not interfere with speech, swallowing, or breathing.

It is yet another object to provide an intraoral controller which permits feedback to the user.

SUMMARY OF THE INVENTION

For years physicians have used electromyography in order to study neuromuscular disorders. It has been found that when a muscle contracts electric fields are generated because of changes in intramuscular electric currents. Muscle contraction causes the movement of charged ions across membrane and myoneural junctions thereby establishing electric fields of varying intensities depending on the degree of muscle contraction. These electric fields, commonly referred to as electromyographic (EMG) signals, may be detected by electrodes which commonly are placed on the skin or inserted into the muscle tissue in the form of a needle. These signals provide useful information to the physician with respect to the neuromuscular condition. Through experimentation it has been found that the tongue muscle is an excellent generator of EMG signals and that the cavity of the mouth provides a somewhat electrically isolated region for detecting such EMG signals. Furthermore, the tongue is a unique muscle in that it is attached only at one end and is able to readily change shape and location within the oral cavity. Also, the tongue, like intrinsic muscles of the hand, has significant fine motor control. It has been found that the low mucosal impedance of the tongue and oral cavity helps keep the EMG signal to noise ratio low.

In accordance with one form of this invention there is provided an intraoral controller including a substrate mountable in the oral cavity. At least one active electrode is attached to the substrate. The active electrode is responsive to EMG signals generated within the oral cavity. A mechanism is provided to transfer signals from the active electrode to a location outside of the oral cavity. Alternatively the electrode or electrodes may be positioned in the oral cavity by a means other than a substrate.

Preferably the intraoral controller is constructed like a dental appliance or splint having a convex side which is in contact with the maxilla or mandible. Preferably four EMG active electrodes are mounted on the side of the splint adjacent to the tongue. These active electrodes receive and detect EMG signals generated by the contraction of the tongue muscle. Ground and reference electrodes may be attached to the convex side of the splint which is in contact with the palate of the maxilla or soft tissue of the mandible.

The preferred means of transmitting EMG signals from the active electrodes is a miniature radio frequency transceiver attached to the splint. The miniature transceiver communicates with an associated transceiver which is connected to an EMG signal processor circuit which is further connected to the device to be controlled such as a means for electrically stimulating the muscles of the upper extremities and hands, a robotic arm or a personal computer. Alternatively, a cable may project through the patient's mouth to provide direct connections to the EMG signal processor from the electrodes.

Preferably there are four independent EMG active electrodes arranged in a diamond pattern on the tongue side of the splint. The active electrodes sense EMG signals from the tongue at various intensities depending on the degree of contraction and location of the tongue with respect to each active electrode. The signals from each active electrode are amplified and integrated, and the integrated signals from opposing electrodes are subtracted and produce a two dimensional vector (X, Y coordinates). In this way the tongue may be used like a joy stick.

It is also preferred to utilize at least one microswitch attached to an edge on the tongue side of the splint to enable and disable the intraoral controller and/or to generate additional control signals. The microswitch may be operated by jaw movement. Also the preferred intraoral controller includes electrotactile feedback electrodes attached to the convex side of the splint which communicate with feedback transducers.

BRIEF DESCRIPTION OF THE DRAWINGS

The subject matter which is regarded as the invention is set forth in the appended claims. The invention itself, however, together with further objects and advantages thereof, will be apparent from the following description taken in conjunction with the accompanying drawings in which:

DESCRIPTION OF THE PREFERRED AND ALTERNATIVE EMBODIMENTS

Figure 1:
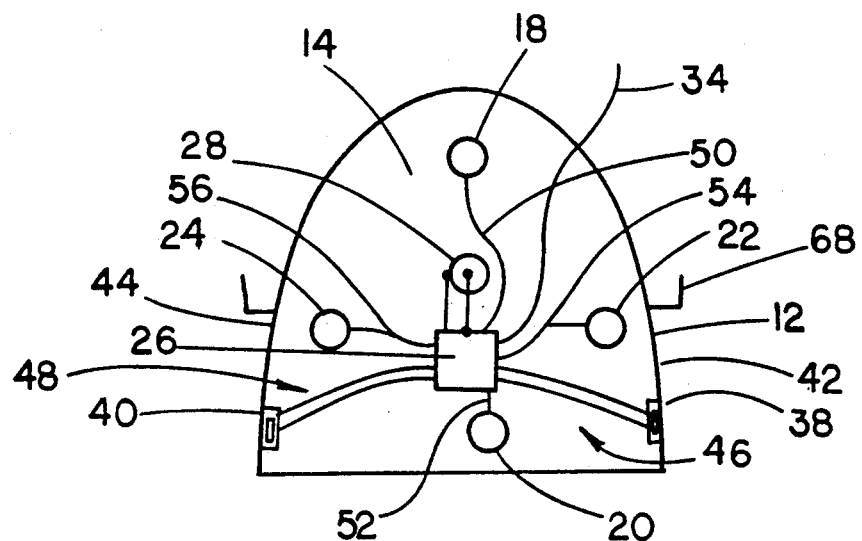
FIG. 1 is a plan view showing the tongue side of the substrate of the intraoral controller of the subject invention and showing wires and an electronics package which are embedded in the substrate.
Figure 2:
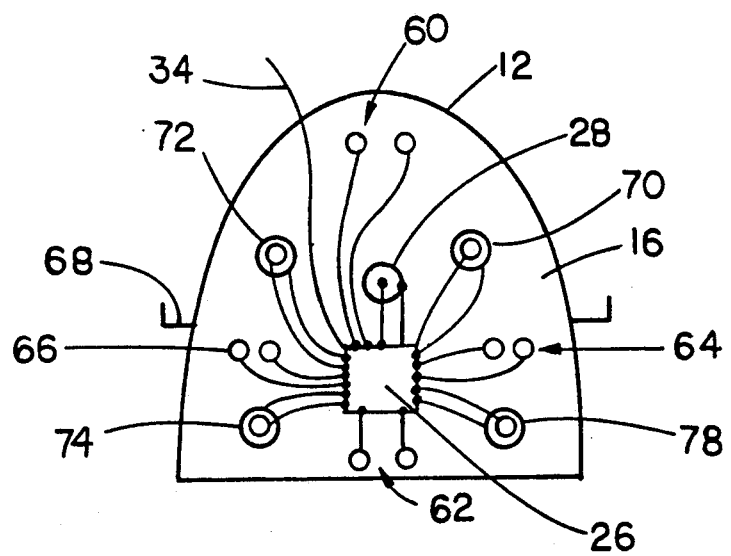
FIG. 2 is a plan view showing the convex side of the substrate of the intraoral controller of FIG. 1.
Figure 3:
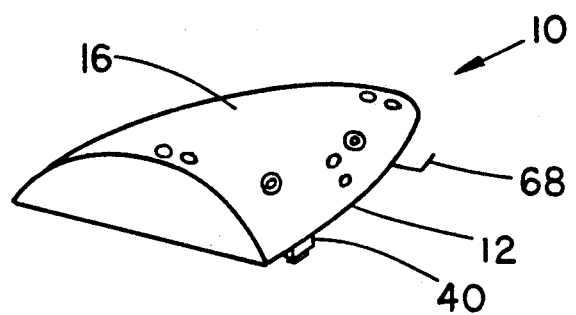
FIG. 3 is a pictorial view of the intraoral controller of FIG. 1 with the interconnecting wires not shown.

Referring now more particularly to FIGS. 1, 2, and 3, which show the preferred embodiment, there is provided intraoral controller 10 including substrate or splint 12. Splint 12 is formed with flat surface 14 and convex surface 16. FIG. 1, being a plan view of the bottom side of the splint adjacent to the tongue, shows active electrodes 18, 20, 22 and 24 mounted on flat surface 14. These sensors are preferably made of stainless steel and are approximately 9 mm in diameter and approximately 1 mm in thickness. Preferably splint 12 is made of a formable acrylic and somewhat resembles a thick orthodontic appliance in shape and in construction.

Figure 6:
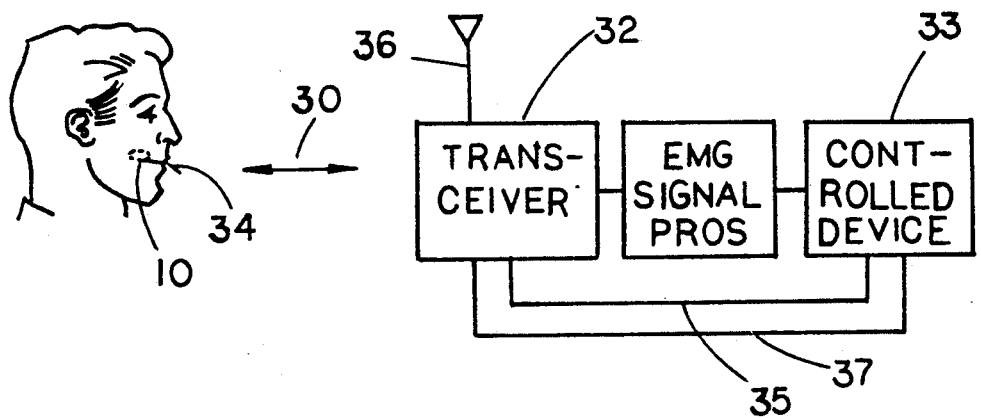
FIG. 6 is a side view of an individual utilizing the intraoral controller of FIG. 1 and a block diagram of an associated external transceiver, EMG processor and device to be controlled.
Figure 7A:
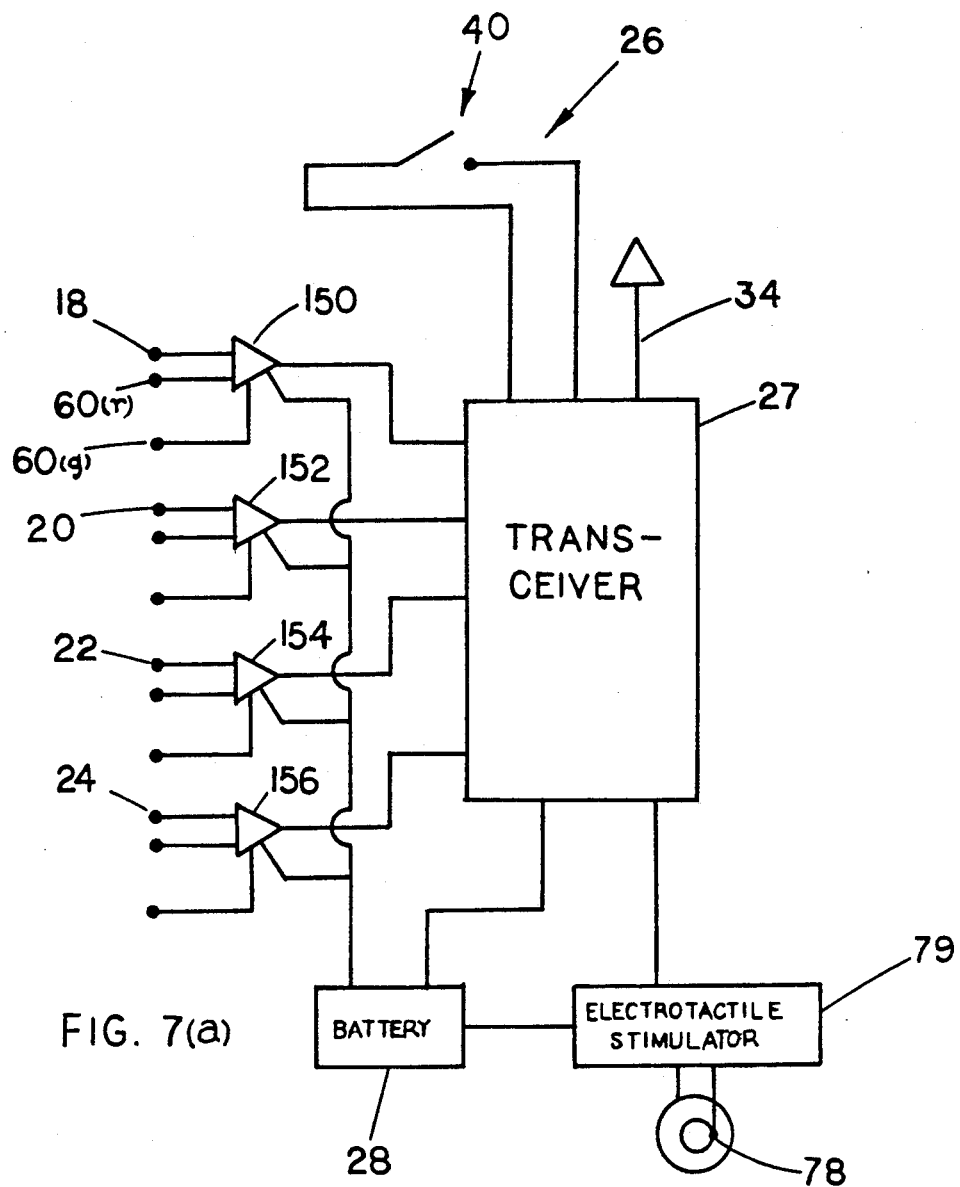
FIG. 7(a) is a block diagram of the circuit in the electronics package of the substrate shown in FIGS. 1 and 2.

Referring to FIG. 1, electronic package 26 and corresponding battery 28 are embedded in the acrylic. A block diagram of the circuit in electronic package is shown in FIG. 7(a). The electronic package includes a transceiver 27 and may be a type known to those skilled in the art similar to that disclosed in U.S. Pat. No. 4,629,424 or U.S. Pat. No. 4,605,927. As indicated by the transmit-receive arrows 30 of FIG. 6, the transceiver 27 within the oral cavity communicates with external transceiver 32. Active electrodes 18, 20, 22 and 24 are connected to electronic package 26 by wires 50, 52, 54 and 56, respectively. The wires are also embedded in the acrylic but are shown in FIG. 1 for ease of understanding.

Figure 4:
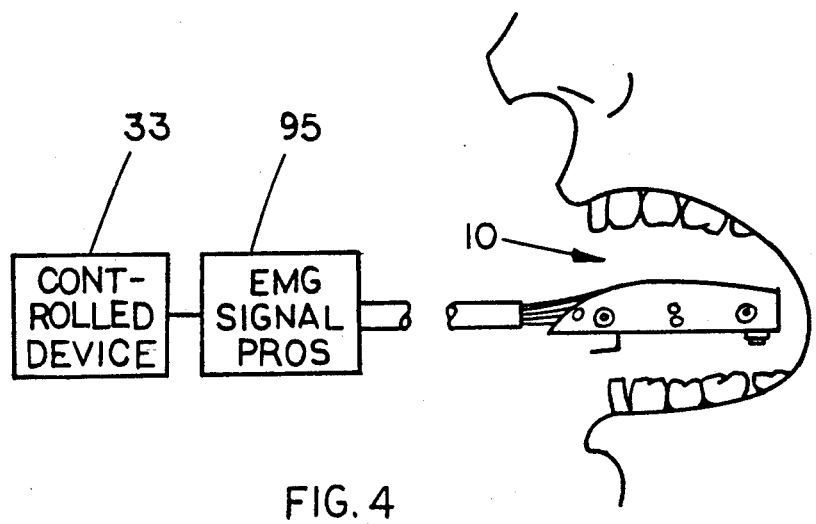
FIG. 4 is a side elevational view of the intraoral controller of FIG. 3 ready to be placed in position in the human mouth but using a direct wiring system from the substrate to an external EMG signal processor rather than through telemetry.
Figure 11:
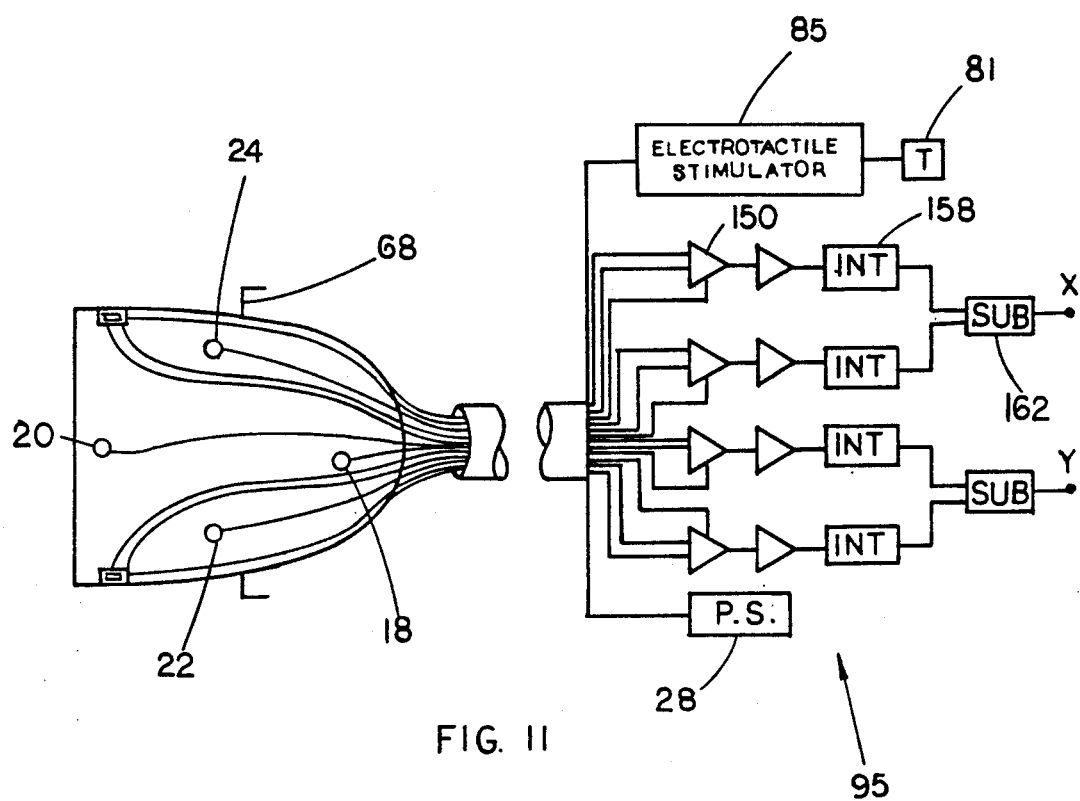
FIG. 11 shows an alternative embodiment of the substrate of the intraoral controller of FIGS. 1, 7(a) and 7(b) showing the flat side.

Alternatively, each active electrode could be directly wired to an external EMG signal processor as generally indicated in FIGS. 4 and 11, thereby eliminating the transceiver and battery. Obviously, however, the user would prefer not to have a group of wires or a cable extending from his or her mouth.

Antenna 34 is attached to transceiver 27 and is in the form of a wire extending slightly beyond surface 14 of the splint. It is preferred that the antenna 34 extend slightly outside of the oral cavity so as not to cause interference with EMG signals. A corresponding antenna 36 is attached to transceiver 32 shown in FIGS. 6 and 7(b).

Miniature mechanical switches 38 and 40 are attached to the flat side of splint 12 along edges 42 and 44, respectively. Switches 38 and 40 may be SX Subminiature Basic Switches available from Microswitch. Switch 38 is connected to electronic package 26 through wires 46 and switch 40 is connected to electronic package 26 through the wires 48. Again the switches may be wired directly to an EMG signal processor as shown in FIGS. 4 and 11. Switches 38 and 40 may be activated by jaw movement, i.e. mating of the teeth and/or side movement of the jaw and may be used to enable and disable the intraoral controller and/or to send additional data to transceiver 32 and on to the controlled device through wires 35 and 37.

Figure 5:
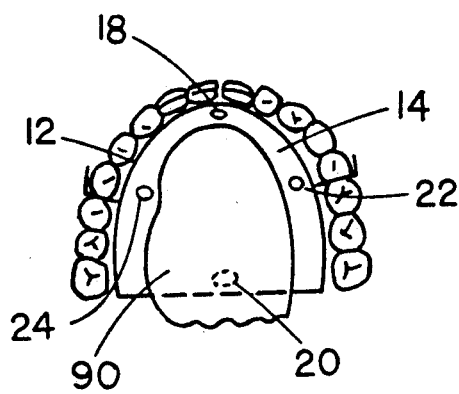
FIG. 5 is a partial view of the upper portion of the mouth and substrate of the intraoral controller which is attached to the teeth.

Referring now more particularly to FIG. 2, which shows the convex side 16 of splint 12, the electronic package 26, battery 28, and antenna 34 again are embedded in the acrylic but are shown for ease of understanding. Pairs of reference and ground electrodes 60, 62, 64 and 66, which preferably are made of stainless steel, are embedded in convex surface 16 and protrude therefrom. There are at least two fasteners 68, each of which is adapted to be wedged between the wearer's teeth, as shown in FIG. 5, to firmly hold the splint in the mouth and maintain contact between the electrodes which are mounted on the convex surface of the splint and the maxilla 104. Each reference and ground electrode is in turn connected to the electronic package 26. Alternatively, the reference and ground electrodes may be directly wired to the EMG signal processor as shown in FIG. 11.

Four electrotactile feedback electrodes 70, 72, 74 and 78 are connected to the convex side 16 of the splint. The electrotactile electrodes are better seen in reference to FIG. 8 which shows an inner metallic disk 80 surrounded by outer metallic ring 82 thereby leaving space 84 between the ring and disk. Disk 80 is connected to electronic package 26 and ring 32 is also connected to electronic package 26 through wires 86 and 88, respectively. When a feedback signal from transceiver 32 is generated and received by transceiver 27, an electric current passes between disk 80 and ring 82 through the moist mucosa of the palate which occupies space 84 between the disk 80 and ring 82, thereby providing a stimulus to the mucosa. By utilizing four electrotactile electrodes, feedback information for each of the four active electrodes is provided. Preferably the electrode 80 and ring 82 are made of stainless steel. Each electrotactile electrode may be directly wired to a known electrotactile stimulator circuit 85 as shown in FIG. 11. A typical electrotactile stimulator is Myocare Plus made by 3M Company. More thorough discussions of electrotactile feedback and stimulators are set forth in an article in *Bulletin of Prosthetic Research*, BRP10-33 (Vol. 17, No. 1), Spring 1980, titled Electrotactile Stimulation Relevant to Sensory-Motor Rehabilitation—A Progress Report by Solomonow and Lyman, pg. 63-72, and in an article from *Orthopedics*, Vol. 7, No. 7, July 1984, pg. 1161-69 titled External Control of Rate, Recruitment, Synergy and Feedback in Paralyzed Extremities by Solomonow et al.

Referring now to FIG. 5, the user's tongue 90 is shown in a position below the flat side 14 of splint 12. The tongue is free to move in any direction with respect to active electrodes 18, 20, 22 and 24. It has been demonstrated that when the tongue is moved forward and the tongue muscle is contracted by pressing it against the front upper teeth or the anterior flat surface 14 of the splint, active electrode 18 detects higher amplitude EMG signals than its corresponding active electrode 20. When the tongue is moved backward toward the posterior flat surface of the splint and is contracted, active electrode 20 detects higher amplitude EMG signals than electrode 18. Curiously, when the tongue is moved to the right toward electrode 24 and is contracted, electrode 22 detects higher amplitude EMG signals than electrode 24, and when the tongue is moved to the left toward electrode 22 and is contracted, electrode 24 detects higher amplitude EMG signals than electrode 22.

Figure 7B:
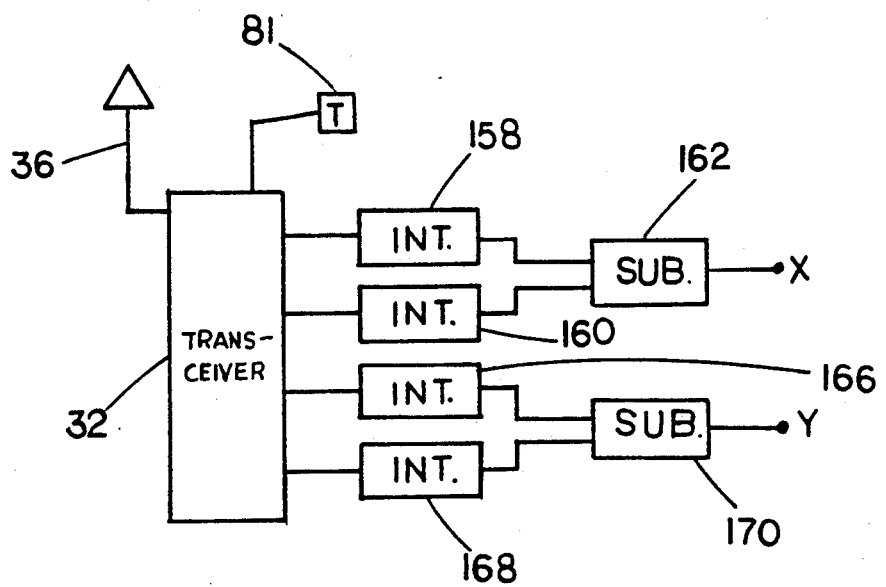
FIG. 7(b) is a block diagram of the circuit located outside of the oral cavity used in conjunction with the circuit of FIG. 7(a).
Figure 10:
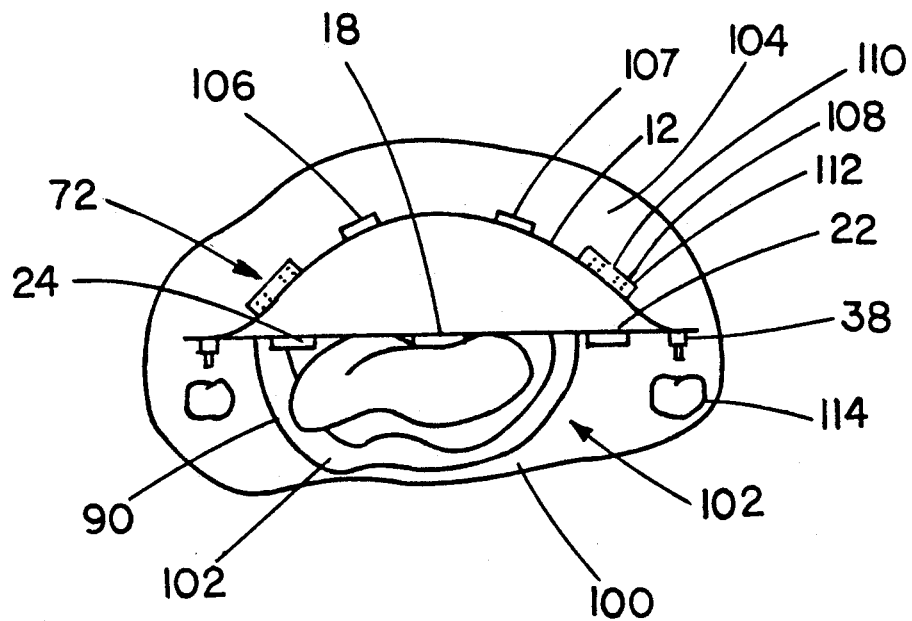
FIG. 10 is a partial front view of the mouth showing the intraoral controller mounted in the oral cavity with the tongue contracted thereby generating an electric field.
Figure 13:
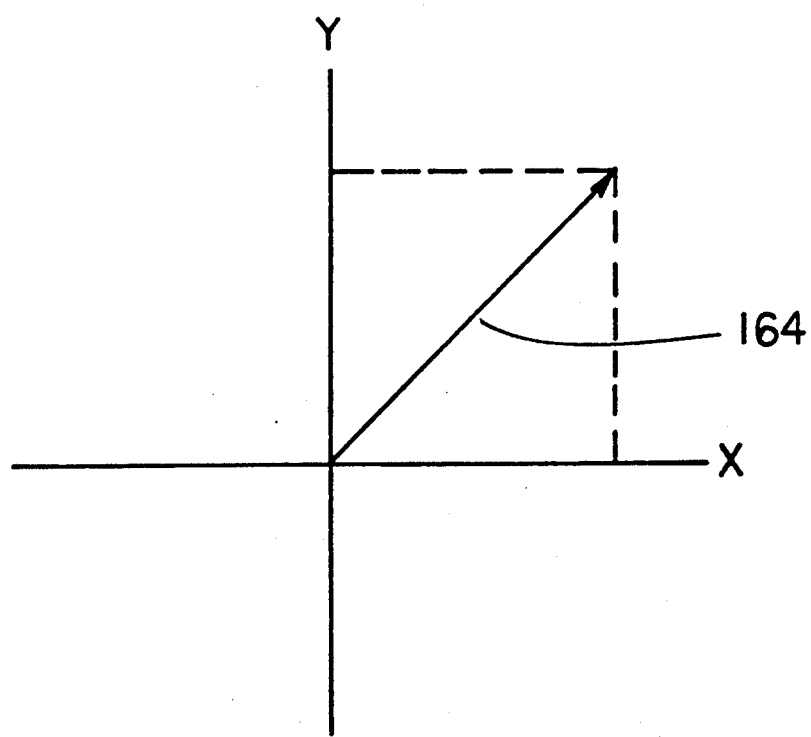
FIG. 13 shows a vector in X and Y coordinates generated as a result of processing EMG signals from the oral controller of the subject invention.

FIG. 10 shows a front view of splint 12 mounted in oral cavity 100 with portions removed for ease of understanding. The size of the electrodes on splint 12 and their extension above the surface of the splint have been exaggerated so that they can more easily be seen. Contraction of the muscles of tongue 90 generates EMG signals in the form of an electric field generally indicated as 102. As previously described in reference to FIG. 5, as the tongue moves forward and backward and left and right and is contracted active electrodes 18, 20, 22 and 24 detect various intensities of the electric field depending on the position of the tongue and the degree of contraction. As shown in FIG. 10, the tongue is pressing forward and to the right so that electrode 18 will detect stronger EMG signals than its opposing electrode 20 (not shown in FIG. 10) and electrode 22 will detect stronger EMG signals than its opposing electrode 24. After the EMG signals are processed by the circuits shown in FIGS. 7(a) and 7(b) or in FIG. 11, a two dimensional vector, i.e. having amplitude and direction, such as the vector shown in FIG. 13, is generated. A discussion of the circuits shown in FIGS. 7(a), 7(b) and 11 is set forth below. This two dimensional vector may be used to control various items and devices such as a electrical stimulator for the arms and hands, artificial limbs, or even an automobile.

Again referring to FIG. 10, the maxilla 104 makes contact with reference electrode 106 and ground electrode 107. Furthermore the soft tissue fits between the outer ring and the inner disk of each of the electrotactile feedback electrodes 72. Thus the soft tissue fills into region 108 between disk 110 and outer ring 112. Microswitch 38 is mounted above lower tooth 114 so that the lower tooth may open and close the microswitch, thereby enabling and disabling the intraoral controller and/or sending additional signals to be processed.

Figure 9:
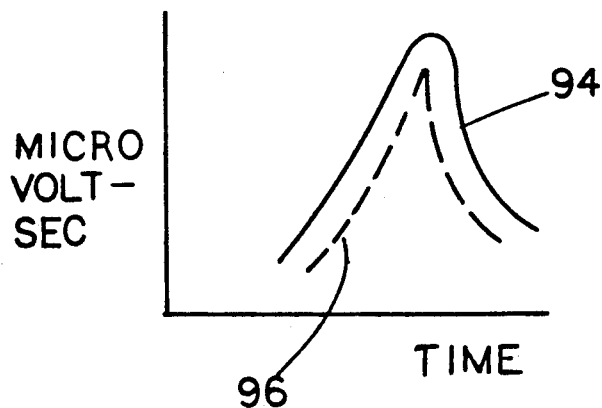
FIG. 9 shows a graph of integrated EMG signals from two sets of active and reference electrodes.

FIG. 9 shows typical integrated wave forms taken from a EMG signal processor showing a difference between the amplitude of the EMG signals between left and right or between forward and rear active electrodes depending on the movement and contraction intensity of the tongue muscle. Line 94 represents the output from an electrode which is detecting the most intense EMG signals and line 96 represents its corresponding sensor which detects lesser EMG signals. These EMG signals which are detected by the active electrodes 18, 20, 22 and 24 are transmitted either via telemetry by the use of transceiver 27 to external transceiver 32 as shown in FIGS. 6, 7(a) and 7(b) or through wires which are connected to the electrodes directly to EMG signal processor as shown in FIGS. 4 and 11. An EMG analyzer such as the Myoexerciser, commercially available from the Verimed Company, may be used in conjunction with known subtraction circuits. A general discussion of EMG is set forth in *Practical Electromyography*, Second Edition, edited by Ernest W. Johnson, with Chapter 14 being dedicated to discussions of the EMG instrumentation.

Referring now more particularly to FIG. 7(a) which is a block diagram of the circuit of the electronics package indicated as item 26 in FIGS. 1 and 2 plus battery/power supply 28, a plurality of high impedance differential amplifiers 150, 152, 154 and 156 are provided. Each differential amplifier includes inputs for active, reference and ground electrodes which are located on the substrate as shown in FIGS. 1 and 2. For simplification, only ground electrode 60(g) and reference electrode 60(r) are labeled. Active electrode 18, reference electrode 60(r) and ground electrode 60(g) are connected to differential amplifier 150, the output of which is connected to transceiver 27. Transceiver 27 is coupled to external transceiver 32 through antennas 34 and 36. The signal from differential amplifier 150 is integrated by integrator 158 preferably with a ½ second time constant. The signal from differential amplifier 150 which receives the EMG signals from active electrode 20 and its associated ground reference electrode is integrated by integrator 160. The integrated signals from integrators 158 and 160 are subtracted by subtraction circuit 162 thereby generating the X component of vector 164 shown in FIG. 13. The EMG signal from active electrode 22 is integrated by integrator 66 and the EMG signal from active electrode 24 is integrated by integrator 168. These integrated signals from integrators 166 and 168 are subtracted through subtraction circuit 170 thereby forming the Y component of vector 164 as shown in FIG. 13.

Switch 40 is shown in FIG. 7(a) for enabling and disabling the circuit shown in FIG. 7(a) and the circuit shown in FIG. 7(b). A second switch 38 is also utilized but for simplification purposes is not shown. These switches 38 and 40 may also be used to supply additional data to the device to be controlled, 33 as shown in FIGS. 6, in the case of the telemetry operation, and in FIG. 4 in the case of a direct wiring from the mouth to the EMG signal processing circuitry.

Figure 8:
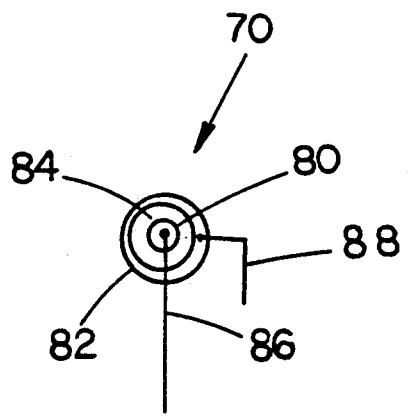
FIG. 8 is a plan view of one of the electrotactile electrodes of FIG. 2 shown in more detail.
Figure 12:
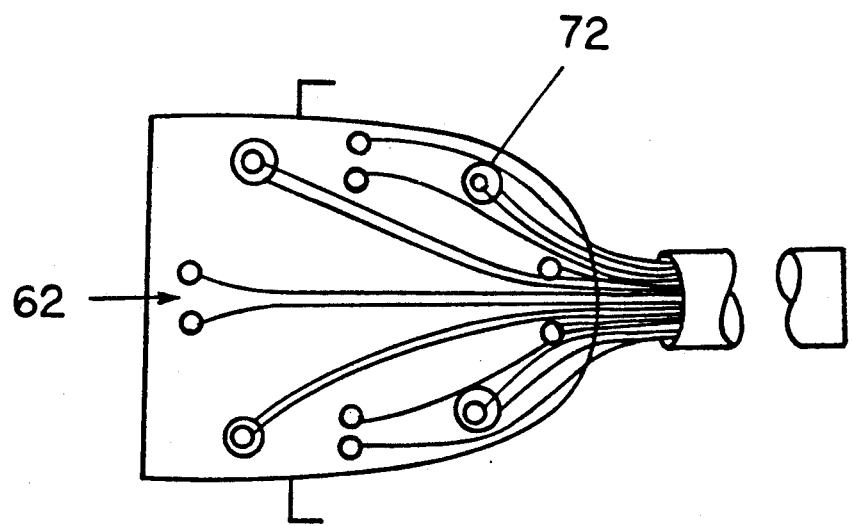
FIG. 12 shows the convex side of the substrate of the intraoral controller of FIG. 11.

Electrotactile feedback electrode 78 is connected to electrotactile stimulator 79 as shown in FIG. 7(a) which in turn is connected to transceiver 27. Electrotactile stimulator 79 will come on in response to a signal generated by transducer 81 shown in FIG. 7(b) through transceiver 32 and transceiver 27, thereby causing a current to flow between disk 80 and ring 82 as shown in FIG. 8, thus providing feedback to the user. There are four electrotactile feedback electrodes connected to the convex side of the substrate as shown in FIG. 2, however for simplification purposes only a single electrotactile feedback electrode is shown in FIG. 7(a). The circuitry shown on the right side of FIG. 11 will operate in a similar fashion to the circuitry shown in FIGS. 7(a) and 7(b) except that the transceivers have been eliminated and that the electrodes and switches have been hard wired to EMG signal processor circuitry, as generally indicated by arrow 95, and the electrotactile stimulator 85 is no longer mounted on the substrate. Electrotactile stimulator 85 is commercially available, however the miniaturized version 7 shown in FIG. 7(a) is not known to be commercially available in miniature form however it is believed that it is within the preview of one of ordinary skill in the art to miniaturize the circuit of the electrotactile simulator using known integrated circuit techniques. It should be noted that reference and ground connections as well as connections to electrotactile simulator 85 are shown in FIG. 11 even though their corresponding electrodes are actually mounted on the convex side of the substrate as shown in FIG. 12.

It has been found, by utilizing a crude prototype device of the intraoral controller described herein, detectable amplitude differences between opposing electrodes caused by tongue movement may be measured. By using four sensors in a diamond pattern, a two dimensional vector with two degrees of freedom may be generated. It has further been found that the tongue may also balance the EMG signals as measured by opposing active electrode by movement toward the middle of the controller in a somewhat resting position. Since the intraoral controller is an analog device, if the tongue is pushed very hard forward a higher amplitude EMG signal is detected than if the tongue is only pushed slightly forward.

Thus an analog intraoral controller which detects different intensities of EMG signals is provided which is tongue and jaw operated, is hidden against the roof of the mouth, may be wireless, does not interfere with speech, swallowing, or breathing and may provide feedback to the user.

From the foregoing description of the preferred embodiments in the invention, it will be apparent that mary modifications may be made therein without departing from the true spirit and scope of the invention.

I claim:

1. An intraoral device comprising:
   a substrate adapted to be mounted in the oral cavity;
   at least one floating active electrode attached to said substrate; said active electrode sensing electric field generated within the oral cavity; said fields being electromyographic signals generated by the movement and contraction of the tongue; said active electrode not being in continuous contact with the tongue; a detector receiving signals from said active electrode.

2. An intraoral device as set forth in claim 1 further including means for transmitting signals from said at least one active electrode to a location remote from the oral cavity.

3. An intraoral device as set forth in claim 1 wherein said substrate has at least two active electrodes attached thereto.

4. An intraoral device as set forth in claim 3 further including a reference electrode associated with each active electrode; each reference electrode attached to said substrate.

5. An intraoral device as set forth in claim 4 further including a ground electrode associated with each reference electrode; each ground electrode attached to said substrate.

6. An intraoral device as set forth in claim 1 wherein said substrate has a convex side and another side; said another side adapted to be adjacent to the tongue; four active electrodes attached to said another side; at least one reference electrode attached to said convex side; said convex side adapted to contact the maxilla; whereby said active electrodes detect electromyographic signals generated by neuromuscular activity of the tongue muscle.

7. An intraoral device as set forth in claim 1 further including at least one switch attached to said substrate for enabling and disabling said intraoral device.

8. An intraoral controller as set forth in claim 1 wherein each of said at least one active electrode being wired to an external EMG processor.

9. An intraoral device as set forth in claim 1 further including a telemetry device attached to said substrate; said at least one active electrode being connected to said telemetry device.

10. An intraoral device as set forth in claim 9 wherein said telemetry device includes a transceiver and a battery attached thereto.

11. An intraoral device as set forth in claim 1 wherein said substrate has a substantially flat side and a convex side; four active electrodes attached to said flat side of said substrate in somewhat of a diamond configuration; corresponding ground and reference electrodes attached to the convex side of said substrate.

12. An intraoral device as set forth in claim 1 further including at least one electrotactile feedback electrode connected to said substrate.

13. An intraoral device as set forth in claim 12 wherein said electrotactile feedback electrode is in contact with tissue within the oral cavity; said feedback electrode includes a disk and a ring surrounding said disk; said disk and said ring are connected to a source of electric current whereby electrical stimulation of the tissue may occur.

14. An intraoral device comprising:
at least one floating active electrode received in the oral cavity;
at least one reference electrode contacting a portion of the tissue surrounding the oral cavity;
said active electrode being responsive to electromyographic signals generated by the movement and contraction of the tongue muscle; said active electrode not being in continuous contact with the tongue; a transmitter for transmitting said signals detected by said active electrode to a position remote from the oral cavity.

15. An intraoral device comprising:
first and second pairs of floating device electrodes located in the oral cavity; said active electrodes adapted to sense EMG signals in the oral cavity generated by the movement and contraction of the tongue;
a first circuit for determining the difference in amplitude of EMG signals between the active electrodes of said first pair;
a second circuit for determining the difference in amplitude of EMG signals between the active electrodes of said second pair; said active electrodes not being in continuous contact with the tongue.

16. An intraoral device as set forth in claim 15 wherein each active electrode of a pair is located across from its corresponding active electrode.

17. An intraoral device as set forth in claim 16 wherein the amplitude of EMG signals sensed by said active electrodes is a function of the contraction of the tongue and its location with respect to said active electrodes.

18. An intraoral device as set forth in claim 17 further including a substrate; said active electrode being located on said substrate.

19. An intraoral device as set forth in claim 15 further including reference electrodes; means for comparing the signal on a reference electrode to the EMG signal on a corresponding active electrode.

20. An intraoral device as set forth in claim 15 further including a differential amplifier connected to each active electrode, and integrator in signal relationship with each of said amplifiers; a first subtraction circuit connected to each integrator associated with signals from said first pair of active electrodes; a second subtraction circuit connected to each integrator associated with said second pair of active electrodes whereby two dimensional vectors are derived from the outputs of said subtraction circuits as a function of the various intensities of EMG signals on each of said active electrodes.

21. An intraoral device as set forth in claim 20 further including telemetry devices located between said amplifiers and said integrators.

22. An intraoral device as set forth in claim 20 wherein said amplifiers are connected in a circuit relationship to said integrators.

23. An intraoral device as set forth in claim 15 further including at least one on-off switch received inside the oral cavity.

24. An intraoral device as set forth in claim 15 further including feedback means; said feedback means including at least one feedback electrode received in the oral cavity; a transducer located outside of said oral cavity in signal relation with said feedback electrode.

25. An intraoral device as set forth in claim 24 wherein said at least one feedback electrode includes four electrotactile feedback electrodes; means to supply current to each of said four electrotactile feedback electrodes.

26. A method for utilizing EMG signals produced by the movement and contractions of the tongue muscle comprising the steps of:
detecting EMG signals at least two locations in the oral cavity utilizing detectors; said detectors not being in continuous contact with the tongue;
subtracting the amplitude of EMG signals detected at a first location from the amplitude of EMG signals detected at a second location.

27. A method as set forth in claim 26 further including the steps of detecting EMG signals at at least four locations within the oral cavity; subtracting the amplitude of EMG signals detected at a third location from the amplitude of EMG signals detected at a fourth location.

28. A method as set forth in claim 27 further including the step of integrating EMG signals detected at each location.

29. A method as set forth in claim 27 further including the step of providing a reference signal corresponding to each location where EMG signals are detected.

30. A method as set forth in claim 27 further including the step of generating a two dimensional vector as a result of said subtractions for providing control.

31. A method as set forth in claim 26 further including the step of providing feedback information to a location within the oral cavity.

32. A method as set forth in claim 26 further including the step of transmitting detected EMG signals from said oral cavity to a location remote from said oral cavity.

* * * * *